United States Patent
Buscayret

Patent Number: 5,824,102
Date of Patent: Oct. 20, 1998

[54] TOTAL KNEE PROSTHESIS

[76] Inventor: Christian Buscayret, 3bis Boulevard des Arceaux, 34000 Montpellier, France

[21] Appl. No.: 897,533
[22] Filed: Jul. 21, 1997

Related U.S. Application Data

[63] Continuation of Ser. No. 347,381, Jan. 12, 1995, abandoned.

[30] Foreign Application Priority Data

Jun. 19, 1992 [FR] France ................................. 92 07843

[51] Int. Cl.⁶ .................................................... A61F 2/38
[52] U.S. Cl. .............................................................. 623/20
[58] Field of Search ............................................. 623/18, 20

[56] References Cited

U.S. PATENT DOCUMENTS

| | | | |
|---|---|---|---|
| 4,136,405 | 1/1979 | Pastrick et al. | 623/20 |
| 4,219,893 | 9/1980 | Noiles | 623/20 |
| 5,011,496 | 4/1991 | Forte | 623/20 |
| 5,330,534 | 7/1994 | Herrington | 623/20 |
| 5,370,701 | 12/1994 | Finn | 623/20 |

FOREIGN PATENT DOCUMENTS

| | | | |
|---|---|---|---|
| 2276553 | 10/1994 | United Kingdom | 623/20 |

*Primary Examiner*—Michael J. Milano
*Attorney, Agent, or Firm*—Oliff & Berridge, PLC

[57] ABSTRACT

A knee prosthesis includes a tibial implant and a femoral implant. The tibial implant is pivotable with respect to the femoral implant about a substantially horizontal axis to permit a flexion/extension movement of the leg, and about a vertical axis which permits a limited pivoting of the tibia about the vertical axis. The vertical axis, about which the tibial implant pivots, is formed by a stud mounted so as to allow axial sliding, in a bore which serves as a rotational bearing therefor. Further, the vertical axis, about which the tibial implant pivots, is offset towards the front of the knee prosthesis with respect to the horizontal axis and is offset towards the inward side of the knee prosthesis with respect to a longitudinal axis of the tibial implant.

14 Claims, 2 Drawing Sheets

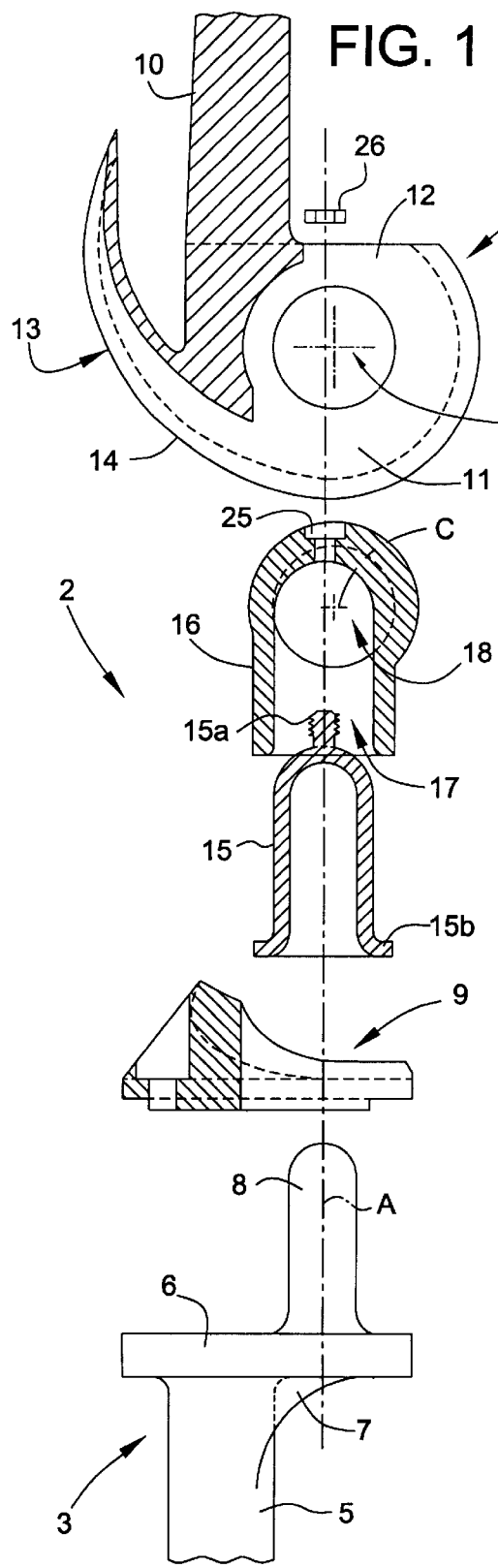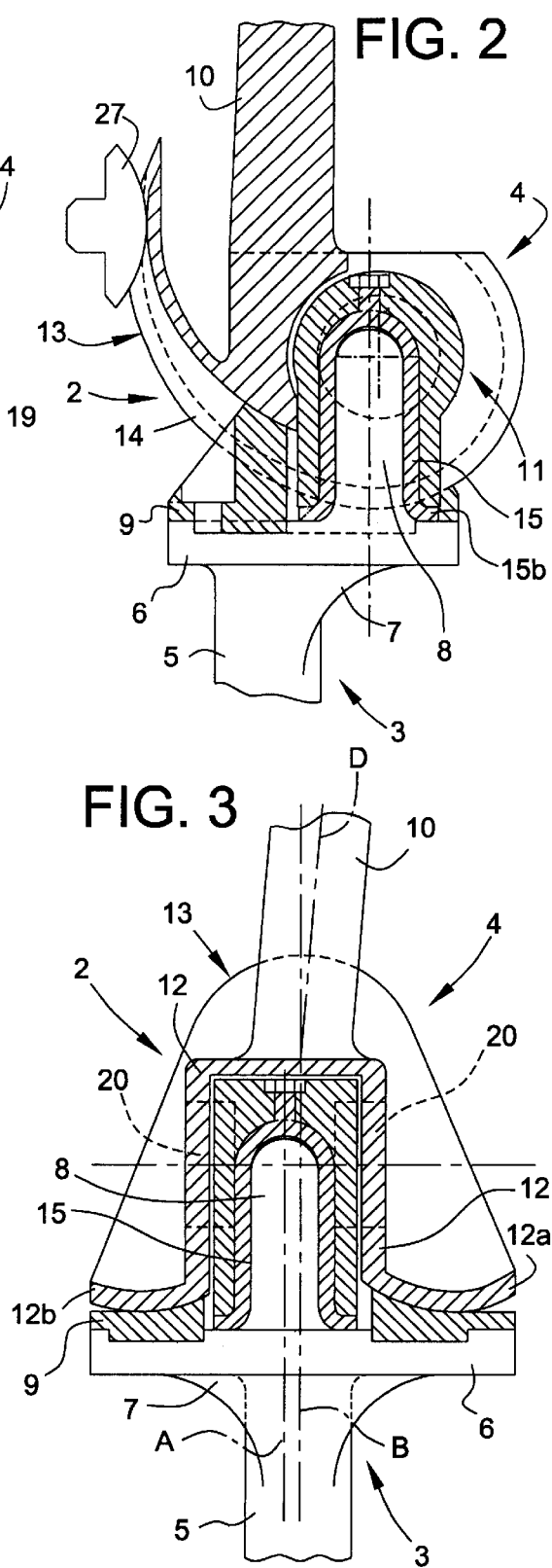

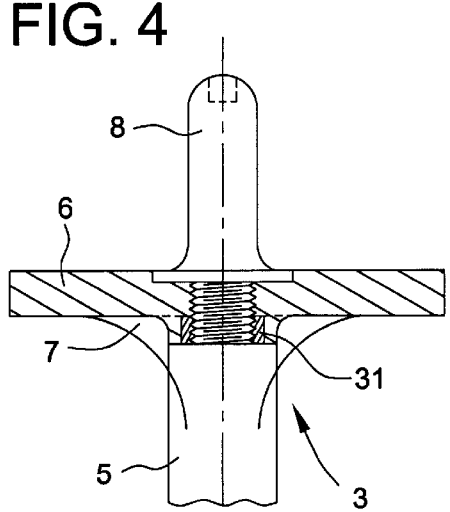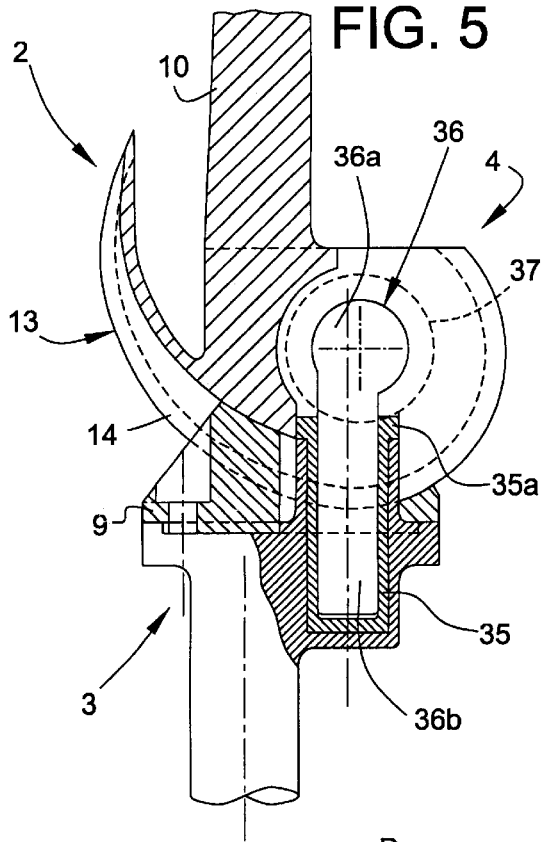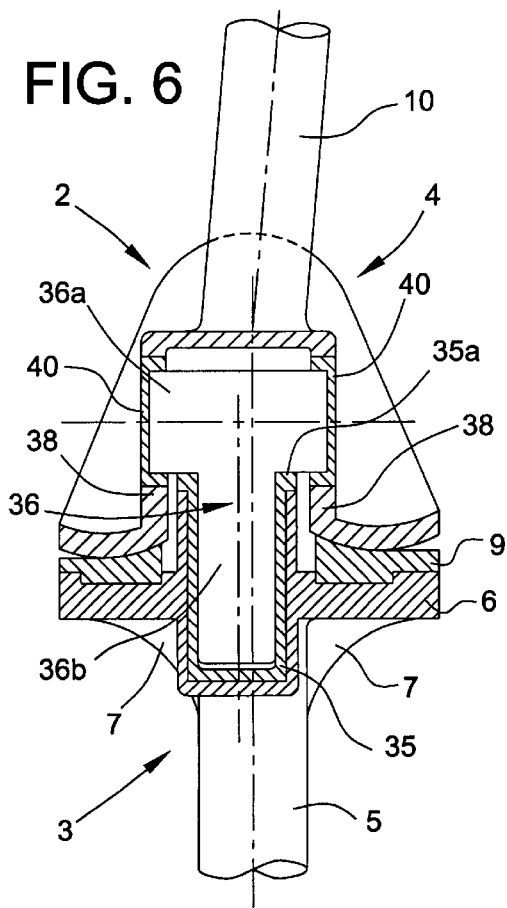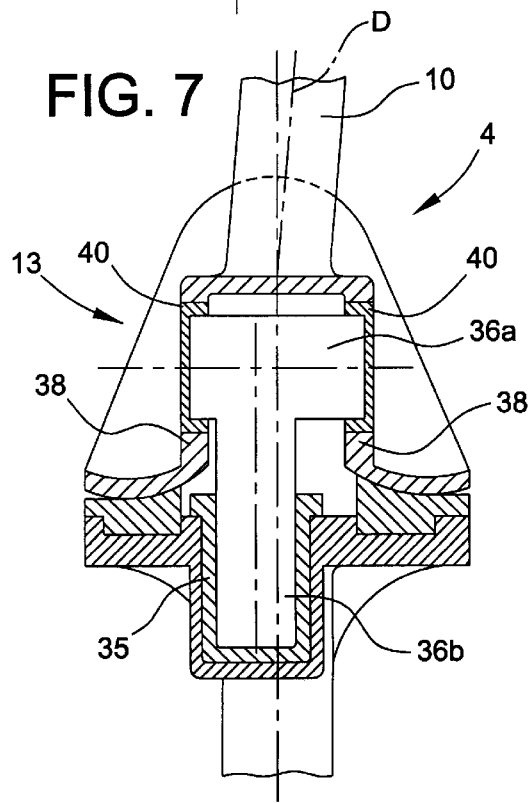

TOTAL KNEE PROSTHESIS

This is a Continuation of application Ser. No. 08/347,381 filed Jan. 12, 1995 now abandoned.

The present invention relates to a total knee-joint endoprosthesis of the type comprising a tibial implant and a femoral implant, the tibial implant being able to pivot with respect to the femoral implant about, on the one hand, a substantially horizontal axis, in order to permit the flexion/extension movement of the leg, and, on the other hand, a vertical axis permitting a limited pivoting of the tibia about its axis.

If clinically necessary, the prosthesis can additionally comprise a patellar implant attached to the natural patella in place of the resected portion thereof and forming a runner sliding along a trochlear shield which the femoral implant forms.

There are a great many knee prostheses of this type, permitting the flexion/extension about a horizontal axis and the internal and external pivoting of the tibia about a vertical axis, and these are described, for example, by the patents FR no. 2 287 895, no. 2 330 375, no. 2 612 767, no. 2 405 064, no. 2 601 873, no. 2 167 381, CH no. 568 066 or U.S. Pat. No. 4,865,606.

It appears in practice that the existing knee prostheses do not optimally respect the kinematic, dynamic and tribology functions of the natural joint.

In fact, in these prostheses, the movement of the femoral condyles on the tibial plate does not correspond completely to the natural movement.

Moreover, the axial and inward pivoting which the tibia performs in the natural joint in the course of the first 50 degrees of flexion of the leg is restored only very imperfectly in its amplitude.

In addition, the stability of the prosthetic joint during its movement is not perfect.

Finally, the bearing load exerted by the weight of the body is distributed essentially on the condylar and glenoid surfaces, which leads to their becoming worn relatively quickly.

The present invention aims to remedy these shortcomings.

To this end, in the prosthesis to which it relates, of the type comprising a tibial implant and a femoral implant, the tibial implant being able to pivot with respect to the femoral implant about, on the one hand, a substantially horizontal axis, in order to permit the flexion/extension movement of the leg, and, on the other hand, a vertical axis which, permitting a limited pivoting of the tibia about its axis, is formed by a stud mounted, with the possibility of axial sliding, in the bore which serves as rotation bearing therefor, characterized in that the vertical axis, about which the tibial implant pivots, is offset inwards and forwards with respect to the horizontal axis about which this same implant pivots during the flexion/extension movement of the leg.

The two axes of pivoting are thus no longer coincident as in the existing prostheses.

The inward offset of the axis of pivoting of the tibial implant about itself, called "medialization" of the axis, makes it possible to increase the amplitude of the anteroposterior movement of the contact zone between the outer femoral condyle and the outer glenoid zone of the tibial plate and, consequently, to diminish the corresponding amplitude of the inner femorotibial contact zone, in a manner which corresponds to the natural joint.

The forward offset of the axis, called "anteriorization", makes it possible to increase the stability of the joint during its movement and to guarantee an amplitude of axial pivoting of the tibial implant which is approximately 30° both in internal and external rotation, this movement approximating to that of the natural movement of the tibia during the flexion/ extension of the leg.

The inward offset of the vertical axis of pivoting of the tibia with respect to the longitudinal mid-axis of the prosthesis can amount to 10 mm, while its forward offset with respect to the axis of pivoting of the tibial implant during the flexion/extension movement of the leg can amount to 8 mm.

The axis of the stem of the femoral implant is advantageously inclined from the top downwards and from the outside inwards with respect to the longitudinal axis of the body of the femoral implant.

In addition, the trochlear groove is delimited by two asymmetrical condyles, the outer one being more prominent than the inner one.

Advantageously, the stud serving as the axis of vertical pivoting of the tibial implant is free to slide with respect to the bore which serves as a bearing therefor, which fact permits a certain axial play of the femoral implant with respect to the tibial implant, approximating the movement permitted by the prosthesis closely to that of the natural joint.

The invention will at any rate be clearly understood from the description which follows, reference being made to the appended diagrammatic drawing which represents, by way of nonlimiting examples, several embodiments of the knee prosthesis to which it relates.

FIG. 1 is an exploded anteroposterior longitudinal sectional view thereof, according to a first embodiment;

FIG. 2 is a similar view thereof, assembled;

FIG. 3 is a longitudinal sectional view thereof, assembled, in a cutting plane perpendicular to the cutting plane according to FIGS. 1 and 2;

FIG. 4 is a longitudinal sectional view of an alternative embodiment of the tibial implant;

FIGS. 5 and 6 are views, which are similar to FIGS. 2 and 3 respectively, of a second embodiment of this prosthesis; and FIG. 7 is a view, similar to FIG. 6, of an alternative embodiment of the prosthesis.

FIGS. 1 to 3 represent, at different angles, a first knee-joint prosthesis 2, comprising a tibial implant 3 and a femoral implant 4, in which the tibial implant 3 can pivot with respect to the femoral implant 4 about, on the one hand, a substantially horizontal axis, in order to permit the flexion/extension movement of the leg, and, on the other hand, a vertical axis permitting a limited pivoting of the tibia about its axis.

The tibial implant 3 comprises a stem 5 for its anchoring in the medullary cavity of the tibia, a horizontal plate 6 whose connection to the stem 5 is reinforced by two oblique ribs 7 directed rearwards, a stud 8 of vertical axis A which is offset to the inside of the prosthesis 2 with respect to the longitudinal mid-axis B of the tibial implant 3, and an insert 9 made of material promoting sliding, such as high-density polyethylene, which is mounted on the plate 6 by dovetail assembly. The dovetail system can be replaced by simple assembly by engagement and screwing.

The upper face of the lateral parts of the insert 9 delimits the glenoid surfaces of the joint, while its central part, which is bulged, is intended to slide in the trochlear groove of the femoral implant 4.

The femoral implant comprises a stem 10 for its anchoring in the medullary cavity of the femur, a central recess 11 which is in the form of a sector of a circle and is delimited by two lateral walls 12, and whose opening is continued via two bulged walls 12a, 12b forming the condylar surfaces and a trochlear shield 13 in which the trochlear groove 14 is arranged.

The prosthesis 2 also comprises a sheath 15 which is made of a material promoting sliding and is intended to be engaged on the stud 8, and a central assembly piece 16 which is drilled with a longitudinal blind cavity 17 permitting its engagement on the sheath 15, with the sheath being placed in contact against the wall of the cavity. The assembly piece 16 comprises two coaxial horizontal bores 18 formed in its lateral faces. The axis of the cavity 17, coincident with the axis of the stud 8, is offset forwards with respect to the axis C of the bores 18.

The sheath 15 comprises a threaded axial nipple 15a intended to be engaged through a counterbored hole 25 formed in the piece 16 and to receive a nut 26, for its connection to the piece 16.

As is shown in FIG. 2, the bores 18 are intended to coincide with two bores 19 drilled in the lateral walls 12 and to receive two coaxial journals 20 constituting the horizontal axis of pivoting of the tibial implant 3. The journals 20 can be joined to the femoral implant 4 by screwing or interlocking.

According to another characteristic of the invention, the axis D of the stem 10 of the femoral implant is inclined from the top downwards and from the outside inwards, forming an angle of the order of 40 with the longitudinal axis of the body of the femoral implant. In addition, the outer condylar surface 12a is more prominent than the inner condylar surface 12b, that is to say the one 12a extends further down than the one 12b.

The stud 8 is free to slide with respect to the sheath 15 and the central assembly piece 16, which fact permits a certain axial play of the femoral implant 4 with respect to the tibial implant 3, approximating the movement permitted by the prosthesis 2 closely to that of the natural joint.

In addition, the free end of the stud 8 does not come to bear against the bottom of the sheath 15 when the condylar and glenoid surfaces are in contact, but the sheath 15 comprises a flange 15b at the end opposite the free end of the stud 8, on which flange the central assembly piece 16 comes to bear when the compressive load of the femoral implant 4 is exerted on the tibial implant 3. Thus, this load is distributed not only on the condylar and glenoid surfaces, but also on the sheath 15, the piece 16 and the journals 20. The wearing of these surfaces is consequently reduced.

The prosthesis 2 can additionally comprise a patellar implant 27 attached to the patella in place of the resected portion thereof and forming a runner sliding along the trochlear shield 13.

The ribs 7 are intended to withstand directly the mechanical loads of femorotibial compression which are applied to the tibial plate 6. This arrangement makes it possible advantageously to reduce the thickness of the tibial plate 6 and, consequently, to minimize the thickness of the tibial bone resection to be performed. It additionally makes it possible to free the zone of implantation of the stud 8.

The inward offset of the stud 8, about whose axis the tibial implant 3 is intended to pivot, makes it possible to increase the amplitude of the anteroposterior movement of the contact zone between the outer femoral condyle and the outer glenoid zone and, consequently, to diminish the corresponding amplitude of the inner femorotibial contact zone, in a manner which corresponds to the natural joint.

The forward offset of the axis of the stud 8 with respect to the axis of the journals 20 makes it possible to increase the stability of the joint during its movement and to guarantee an amplitude of axial pivoting of the tibial implant 3 which is approximately 30° both in internal and external rotation, this movement approximating to that of the natural movement of the tibia during the flexion/extension of the leg.

The inclination of the axis of the femoral stem 10 and the asymmetry of the condyles ensure, during the flexion of the knee-joint, an inward rotation of the tibia which is of an amplitude approximating to that which exists in the natural movement.

FIG. 4 shows an alternative embodiment of the prosthesis 2, in which the stud 8 is not in one piece with the tibial implant 3 but is attached thereto by screwing onto the plate 6, with a locking nut 31.

FIGS. 5, 6 and 7 represent a second embodiment of the prosthesis 2. Those elements described hereinabove and which appear once again in this prosthesis are designated, in these figures, by the same reference labels. The tibial implant 3 comprises a blind hole intended to receive a sheath 35 made of material promoting sliding, and the femoral implant 4 receives, in its intercondylar cavity, the central assembly piece 36 which has substantially the shape of a T, the ends of whose horizontal branch 36a are engaged in two coaxial horizontal bores 37 formed in the walls 38 of the femoral implant delimiting the intercondylar cavity, and whose vertical branch 36b, which constitutes the pivot of the tibial implant 3, is engaged without radial play in the blind hole of the tibial implant 3. The branch 36a bears on the flange 35a of the sheath 35 in the alternative embodiment represented in FIG. 6. Two plugs 40, threaded externally and bored on one of their faces, are screwed into the bores 37 and constitute bearings for the pivoting of the piece 36.

The prosthesis 2 according to this embodiment has a less voluminous intercondylar part and, as a result, makes it possible to minimize the bone resection of the intercondylar mass. In addition, the pivot constituted by the branch 36b of the piece 36 is more elongate, which makes it possible to reduce the wearing stress of the sheath 35 engaged thereon.

FIG. 7 represents an alternative embodiment of the prosthesis 2 in which the branch 36b of the piece 36 is distinctly offset from the transverse mid-axis of the branch 36a. Thus, the piece 36 provides for the entire medialization of the axis of rotation of the tibial implant 3, which leads to the centring of the intercondylar block and thus the symmetry of the condyles. In addition, the branch 36b of the piece 36 does not come to bear on the flange 35a of the sheath 35 but instead against the bottom of the sheath 35.

It goes without saying that the invention is not limited to the embodiments described hereinabove as examples, but instead encompasses all alternative embodiments thereof. Thus, the tibial element could comprise means for adjusting the position of the stud, for example of the oblong slot type, with the stud being locked in position by a screw/nut. In addition, intermediate pieces made of material promoting sliding could be provided between the abovementioned journals and the wall of the femoral element serving as a bearing for them, or between the lateral walls of the intercondylar block and the central assembly piece.

It is claimed:

1. A knee prosthesis having a top, a bottom, a front, a rear and inward and outward sides when implanted in a leg of a body, the knee prosthesis comprising:

a tibial implant; and a femoral implant, the tibial implant being able to pivot with respect to the femoral implant about a substantially horizontal axis to permit a flexion/extension movement of the leg, and about a vertical axis to permit a limited pivoting of the tibia about the vertical axis, wherein the vertical axis, about which the tibial implant pivots, is formed by a stud slidingly mounted within a bore provided-in at least one of the femoral and tibial implants which serves as a rotational bearing therefor and which is configured to extend above a tibial plateau of the tibial implant and inside the horizontal articulation, and wherein the vertical axis, about which the tibial implant pivots, is a central longitudinal axis of the stud and is offset towards the front of the knee prosthesis with respect to the horizontal axis and is offset towards the inward side of the knee prosthesis with respect to a central longitudinal axis of the tibial implant.

2. The knee prosthesis according to claim 1 wherein an longitudinal axis of a stem of the femoral implant is inclined from the top of the knee prosthesis downwards and from the outward side of the knee prosthesis inward with respect to a central longitudinal axis of the body of the femoral implant.

3. The knee prosthesis according to claim 1 wherein a trochlear groove of the femoral implant is delimited by two asymmetrical condyles, an outer one of the two asymmetrical condyles being more prominent than an inner one.

4. The knee prosthesis according to claim 1 wherein the forward offset of the vertical axis, about which the tibial implant pivots, is greater than zero and no greater than 8 mm, while the inward offset of the vertical axis, about which the tibial implant pivots, is greater than zero and no greater than 10 mm.

5. The knee prosthesis according to claim 2 wherein an angle which the longitudinal axis of the stem of the femoral implant forms with the central longitudinal axis of the body of the femoral implant is approximately 4 degrees.

6. The knee prosthesis according to claim 1 further comprising a central piece for assembling the tibial and femoral implants and effecting the forward and inward offsets, the central piece including means for guiding the tibial implant with respect to the femoral element about the two non-coincident axes.

7. The knee prosthesis according to claim 6 wherein the tibial implant includes the stud, on which a sheath made of material promoting sliding can be fitted, and which the femoral implant receives, in an intercondylar cavity, and wherein the central piece includes a longitudinal blind cavity that permits engagement of the central piece on the sheath and which constitutes the bore serving as the rotational bearing for the stud, the central piece including two coaxial horizontal bores formed in lateral faces thereof and intended, when the central piece is engaged in the intercondylar cavity, to come into coincidence with two coaxial bores formed in laterals walls of the femoral implant delimiting the cavity and to receive two coaxial journals forming a pivot.

8. The knee prosthesis according to claim 7 wherein the sheath comprises a threaded axial nipple intended to be engaged through a counterbored hole formed in the central piece and to receive a nut for connection to the central piece.

9. The knee prosthesis according to claim 6 wherein the tibial implant comprises a blind hole constituting the bore serving as the rotational bearing for the stud, into which a sheath made of material promoting sliding can be fitted, and wherein the femoral implant receives, in an intercondylar cavity, the central piece which has substantially the shape of a T with ends of the horizontal branch being engaged in two coaxial horizontal bores formed in lateral walls of the femoral implant delimiting the intercondylar cavity, and whose vertical branch, which constitutes the stud is engaged in the blind hole of the tibial implant.

10. The knee prosthesis according to claim 6 wherein a vertical axis at a mid-point of a transverse branch of the central piece is offset with respect to a vertical axis of a vertical branch of the central piece.

11. The knee prosthesis according to claim 7 wherein the sheath comprises at an end a flange on which the central piece comes to bear.

12. The knee prosthesis according to claim 1 further comprising a patellar implant attachable to a patella of the leg in place of a resected portion thereof and forming a runner sliding along a trochlear shield formed by the femoral implant.

13. The knee prosthesis according to claim 1 wherein the tibial implant comprises a stem for anchoring, and a horizontal plate whose connection to the stem is reinforced by two oblique ribs directed to the rear of the knee prosthesis.

14. A knee prosthesis having a top, a bottom, a front, a rear and inward and outward sides when implanted in a leg of a body, the knee prosthesis comprising:

a tibial implant; and a femoral implant, the tibial implant being able to pivot with respect to the femoral implant about a substantially horizontal axis to permit a flexion/extension movement of the leg, and about a vertical axis to permit a limited pivoting of the tibia about the vertical axis, wherein the vertical axis, about which the tibial implant pivots, is formed by a stud slidingly mounted within a bore provided in at least one of the femoral and tibial implants which serves as a rotational bearing therefor, and wherein the vertical axis, about which the tibial implant pivots, is a central longitudinal axis of the stud and is offset towards the front of the knee prosthesis with respect to the horizontal axis and is parallel to and offset towards the inward side of the knee prosthesis with respect to a central longitudinal axis of the tibial implant.

* * * * *